(12) United States Patent
Faraldi et al.

(10) Patent No.: US 7,036,558 B2
(45) Date of Patent: May 2, 2006

(54) METHOD AND SYSTEM FOR EVALUATING LOCAL COMPACTNESS OF A GRANULAR MATERIAL

(75) Inventors: Paolo Faraldi, Sanremo (IT); Silvio Antonioni, Pomarolo (IT); Edoardo Merlone Borla, Candiolo (IT)

(73) Assignee: C.R.F. Societa' Consortile per Azioni, Strada Turin (IT)

( * ) Notice: Subject to any disclaimer, the term of this patent is extended or adjusted under 35 U.S.C. 154(b) by 218 days.

(21) Appl. No.: 10/357,060

(22) Filed: Feb. 3, 2003

(65) Prior Publication Data

US 2004/0000388 A1    Jan. 1, 2004

(30) Foreign Application Priority Data

Jun. 26, 2002   (IT)  .................... TO2002A0556

(51) Int. Cl.
*B22C 19/00*  (2006.01)
(52) U.S. Cl. .................... 164/456; 164/150.1
(58) Field of Classification Search ............... 164/4.1, 164/456, 150.1, 154.1
See application file for complete search history.

(56) References Cited

U.S. PATENT DOCUMENTS 3,784,905 A * 1/1974 Blackwell ................ 324/663
4,550,768 A * 11/1985 McMullen et al. ......... 164/456
5,618,484 A * 4/1997 Mogensen et al. ......... 264/220
5,898,309 A * 4/1999 Becker et al. ............ 324/689
5,900,736 A   5/1999 Sovik et al.
5,996,681 A * 12/1999 Pohlandt .................... 164/456
6,272,932 B1 * 8/2001 Nishida ........................ 73/823

FOREIGN PATENT DOCUMENTS

| DE | 26 27 904 | 1/1978 |
| DE | 197 55 418 | 6/1999 |
| GB | 1 381 921 | 1/1975 |
| JP | 57-187143 | * 11/1982 |
| JP | 5-309442 | * 11/1993 |

* cited by examiner

*Primary Examiner*—Kevin P. Kerns
(74) *Attorney, Agent, or Firm*—Frost Brown Todd LLC

(57) ABSTRACT

An evaluation method in which a capacitive sensor is placed in a region of a container, into which a granular material is fed so as to contact the sensor, and the variation in the impedance of the sensor caused by feeding in the material is evaluated. The method is particularly useful for evaluating the compactness of sand in a formwork for making metal castings. The evaluation system includes a sensor defined by plates sensitive to the variation in the dielectric; and a conditioning and control circuit for indicating the variation in the capacitance of the plates, or more generally the total impedance of the system, when the granular material is fed into the container. In one embodiment, the plates of the sensor are defined by two combs made of conducting material, having two numbers of interlacing segments, and located on a rigid or flexible support.

2 Claims, 2 Drawing Sheets

METHOD AND SYSTEM FOR EVALUATING LOCAL COMPACTNESS OF A GRANULAR MATERIAL

The present invention relates to a method and system for evaluating local compactness of a granular material.

BACKGROUND OF THE INVENTION

Sand casting is one of the methods most commonly used in foundry work, and has been developed over the years so that numerous widely differing ways now exist of obtaining molds for casting highly complex parts of good dimensional accuracy. One of the most advanced methods in this respect is what is known as "Lost Foam Casting".

The common denominator of all sand casting methods is the use of sand as a moldable material to support the metal, and which forms a "negative" of the required casting. In the case of complex molds in particular, however, it is difficult to ensure all the gaps in the pattern (eventually forming the underside recesses or cavities in the finished part) are filled with sand to an adequate degree of compactness. Moreover, in Lost Foam Casting, there are no polymer binders added to the sand, so that the mold depends mainly on the compactness of the sand itself.

To ensure all the hollows are filled completely with sand, mechanical vibration is applied to the pattern and the formwork containing the sand, so that the sand flows into all the cavities and gaps; and complete filling of the formwork must be accompanied by adequate compacting of the sand, the absence of either one of which conditions may impair the quality, and result in rejection, of the finished casting.

At present, the only way of evaluating the compactness of the sand inside the formwork is by characterizing and controlling vibration of the formwork. Such a method, however, being indirect, still does not ensure against individual casting defects caused by inadequate local compactness or filling; which uncertainty, particularly in the case of fairly complex molds, may result in a large number of rejects.

U.S. Pat. No. 5,996,681 describes a casting mold quality control system, in which the molds are measured using proximity sensors to prevent casting defects, but which makes no provision for sand compactness evaluation.

SUMMARY OF THE INVENTION

It is an object of the present invention to eliminate the drawbacks of the known state of the art by providing a compactness evaluation method and system, which provide for locally and directly evaluating the compactness of mold sand, or more generally a granular material inside a container, and which are highly reliable and inexpensive.

According to the present invention, there is provided a method of evaluating local compactness of a granular material inside a container, characterized by comprising the steps of:

setting up a compactness evaluation system comprising a capacitive sensor, and a conditioning and control circuit for conditioning and controlling said sensor and capable of evaluating the variation in impedance of the sensor;

placing said sensor inside a region of said container in which the compactness of said granular material is to be evaluated;

feeding said granular material into said container and into contact with said sensor; and directly evaluating, by means of said circuit, the local compactness of the granular material contacting or in close proximity to said sensor, on the basis of the variation in the impedance of said sensor, and in particular in the capacitive component of said impedance.

More specifically, the variation in impedance is mainly related to the variation in the capacitive component of the sensor, which is directly proportional to the characteristics of the granular material.

Said conditioning and control circuit may be either separate or integrated in the body of the sensor.

The relative compactness evaluation system comprises a capacitive sensor defined by a capacitor in turn defined by two or more plates; and a conditioning and control circuit for conditioning and controlling said sensor; said sensor having a given no-load capacitive impedance component; and the system being characterized in that said sensor comprises an outer surface so shaped as to be positioned, in use, contacting or in close proximity to said granular material; said circuit receiving from said sensor a signal indicating the variation in the capacitive impedance component of the sensor, when said surface contacts or is in close proximity to said granular material, and accordingly indicating the local compactness of said granular material.

Said circuit may also evaluate the resistive and inductive impedance components of said sensor, to obtain a more reliable granular material compactness evaluation by identifying any spurious effects or undesired synergies of various phenomena. For example, a variation in the humidity of the granular material may cause a variation in its dielectric constant, which, however, may be eliminated by measuring resistivity. Contamination of the granular material (carbon residue, metal particles) may also produce spurious signals, but may be counteracted by measuring and appropriately correlating resistive and inductive impedance parameters.

In the case of foundry work, the sensor according to the invention provides for local sand compactness evaluation and supplying a proportional analog signal; and the physical principle on which evaluation is based enables the sensor to be produced in various shapes, sizes, and materials (rigid or flexible) to adapt perfectly to the most critical control regions.

Use of the sensor according to the invention therefore improves process control to reduce the number of rejects, by sand compactness evaluation enabling any badly prepared formworks, preforms, cores or similar to be eliminated from the production line before proceeding to subsequent production stages.

BRIEF DESCRIPTION OF THE DRAWINGS

A number of preferred, non-limiting embodiments of the invention will be described by way of example with reference to the accompanying drawings, in which.

DETAILED DESCRIPTION OF THE INVENTION

Figure 1:
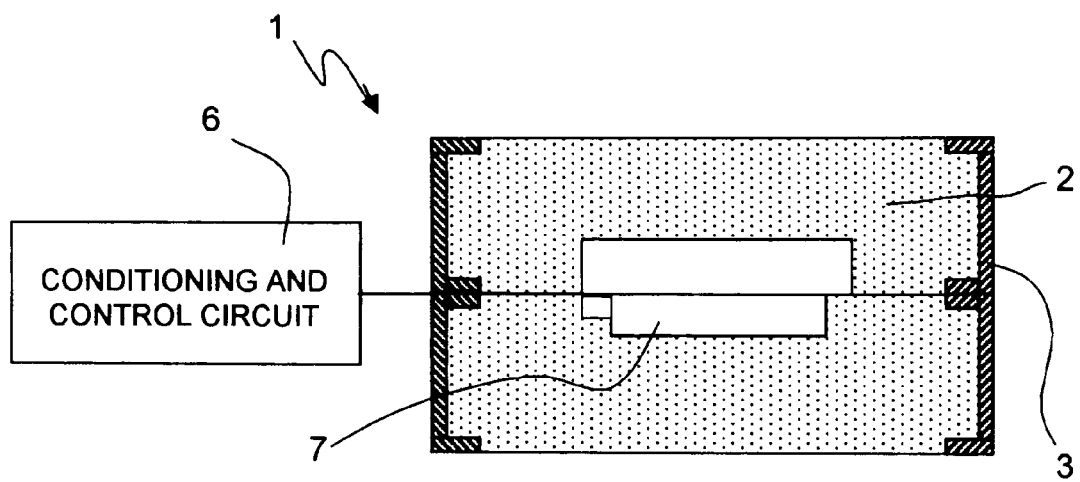
FIG. 1 shows a system of evaluating the compactness of a granular material using a capacitive sensor, in accordance with the invention.

With reference to FIG. 1, number 1 indicates as a whole a system for evaluating the local compactness of a granular material 2 inside a container 3. Evaluation system 1 comprises a capacitive sensor 5; and a circuit 6 for conditioning and controlling sensor 5, and which also indicates the compactness corresponding to the signal received from sensor 5, as explained in detail later on.

By way of example, container 3 may be defined by a formwork containing a pattern 7, and in which a mold for casting molten metal into a part corresponding to pattern 7 is formed in known manner from sand. Sensor 5 is located in a region in which the compactness of the sand is to be evaluated—normally a critical sand fill region; and the sand must be brought into close proximity to or contact with sensor 5.

Operation of evaluation system 1 using capacitive sensor 5 is based on the variation in the electromagnetic characteristics (dielectric constant, electric resistivity, magnetic reluctance or permeability) of a volume of material through which an electromagnetic field flows. Said electromagnetic characteristics are therefore directly relatable to the compactness of the material, as explained later on. The electromagnetic field is induced by, and in an area adjacent to, the two or more plates of sensor 5. And for sensor 5 to be sensitive to variations in electromagnetic characteristics within as large and accessible a space as possible, as opposed to simply the space between the plates, the structure and shape of the plates are such as to emphasize the edge effects, as explained later on.

The electromagnetic field produced by the plates covers a given volume corresponding to the inside of the formwork or mold in which the compactness of the sand is to be evaluated. Examination, in particular, of the capacitive impedance component of the sensor, which is calculated using different equations depending on the geometry of the plates, shows it is directly proportional to the dielectric constant of the medium through which the field travels.

A difference in sand compactness can be described as a variation in the percentage of a volume of space occupied by sand as opposed to ambient air. The dielectric constant of the air/sand mixture can therefore be expressed by the equation:

$$\epsilon = \epsilon_0 \cdot \{S \cdot \epsilon_{rS} + (1-S) \cdot \epsilon_{rA}\}$$

where S is the fraction of volume occupied by sand; $\epsilon_{rS}$ is the dielectric constant of sand; $\epsilon_{rA}$ is the dielectric constant of air (or other aeriform process substance); and $\epsilon_0$ is the dielectric constant of a vacuum.

Since the dielectric constant of sand $\epsilon_{rS}$ differs considerably from that of air (with a 0.1 g/cm$^3$ water content, the dielectric constant of sand is ~6 F/m as opposed to 1 F/m for air), as the volume percentage of sand increases with respect to that of air, the value of the capacitive impedance component of the sensor (directly proportional to s) shows the following pattern:

a sharp initial variation, caused by the first fill;

a further variation, caused by compacting the sand, the volume percentage of which, in fact, goes from 0% to over 70%.

The capacitance value measurement may therefore be normalized, for example, as a function of the compactness of the sand, to obtain a parameter ranging from 0% (sensor in air) to 100% (sensor 5 in fully compacted sand), and which can be calibrated to adapt it to variations in the properties of the granular material (normally sand), due, for example, to different suppliers or variations in environmental conditions. In this respect, measuring the resistive and/or inductive impedance components of the sensor ensures a more reliable evaluation of the compactness of the granular material by identifying any spurious effects (e.g. variation in the humidity of the granular material, contamination by carbon residue or metal particles) or undesired synergies between the above phenomena and compactness of the granular material.

Figure 2:
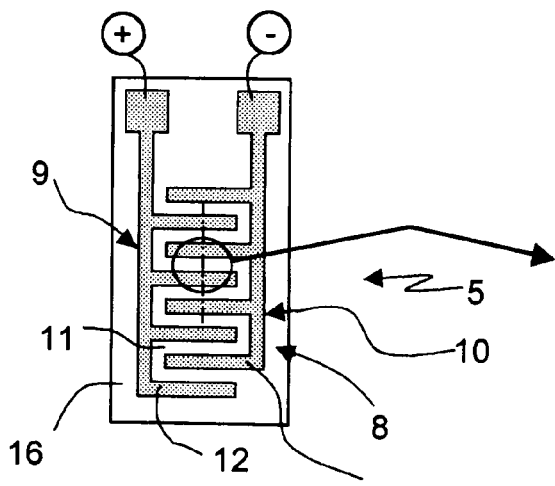
FIG. 2 shows a first geometrical design of the two or more plates constituting the sensitive part of the FIG. 1 system sensor.
Figure 3:
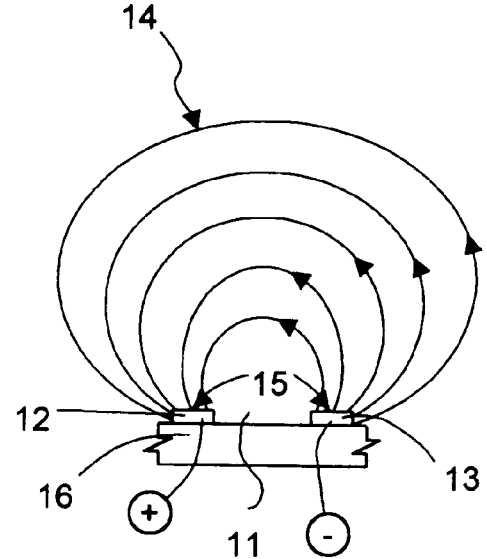
FIG. 3 shows a larger-scale, partial section of a detail in FIG. 2.

With reference to FIGS. 2 and 3, sensor 5 comprises a capacitor 8 defined by two plates 9 and 10, each having an outer surface 15 and fitted to a support 16. Plates 9 and 10 are separated by a dielectric 11, normally air, and are defined by two opposite combs each having a respective number of interleaved straight segments 12 and 13. When supplied with alternating voltage, plates 9 and 10 generate an electromagnetic field comprising an outer electromagnetic field 14 (FIG. 3) close to, and located around surfaces 15 of, plates 9 and 10.

Capacitor 8 is designed to mainly generate electromagnetic field 14 by means of the edge effects of plates 9 and 10. Because of the variation in the dielectric constant of the dielectric effected by electromagnetic field 14, the granular material 2 close to plates 9 and 10 causes a variation in the capacitive impedance component of sensor 5; and the geometry of the plates is designed to maximize the length of the facing conductor portions, while maintaining as small a total area as possible to maximize the capacitive inductance component.

System 1 evaluates the variation in the impedance of sensor 5. Circuit 6 supplies an analog electric signal proportional to the instantaneous impedance of sensor 5 and—since the capacitive impedance component is directly related to compactness—indicating the local compactness of granular material 2. Circuit 6 may also be designed to supply a compactness-proportional signal in real time.

Circuit 6 may also measure the resistive and inductive components of sensor 5, and make corrections to the granular material compactness value.

Figure 4:
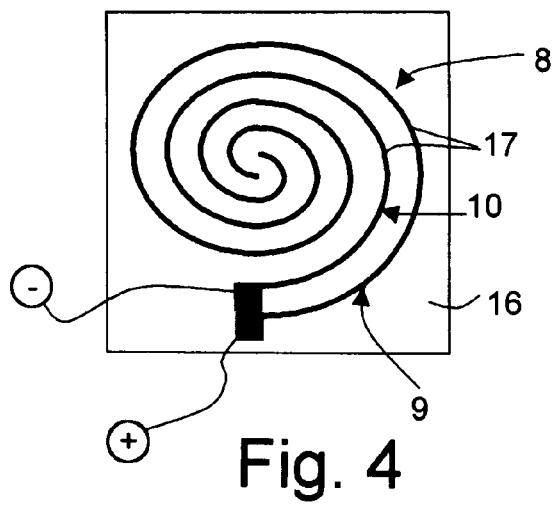
FIGS. 4 and 5 show a further two geometrical designs of the sensitive plates.
Figure 5:
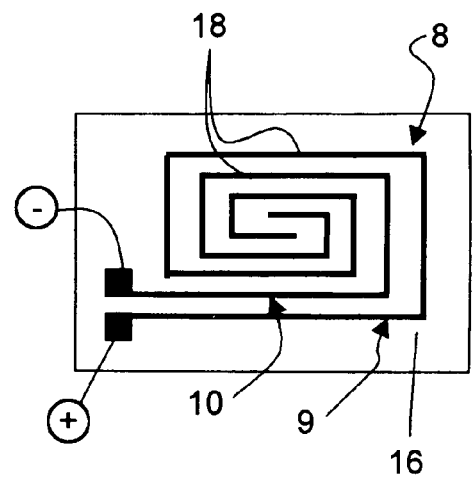

In the FIG. 4 variation, plates 9 and 10 are in the form of two coplanar, concentric spirals defined by circular segments 17. In the FIG. 5 variation, plates 9 and 10 are defined by two coplanar, concentric spirals defined by straight segments 18.

Plates 9 and 10 of capacitor 8 in FIGS. 2–5 may be defined by thin, rigid or flexible plates fitted to a support 16, which may be fitted to or incorporated in a selected region of container 3. Plates 9 and 10 may also be defined by a thick or thin conductive film applied to support 16, which may be defined by a thin adhesive film designed to stick to the selected region of container 3. Finally, plates 9 and 10 may be formed by depositing a thin film directly on container 3 or pattern 7.

Granular material 2 may be defined by sand, or sand 15 mixed with additives and/or binders. Container 3 may be defined by a formwork containing pattern 7, and which is filled with sand to form a mold for a metal casting; or container 3 may be defined by a foundry core mold.

Container 3 may also be defined by a mold containing a cluster of polymer foam for Lost Foam Casting, or a polymer in pellets, or powdered or granular ceramic. Container 3 may also be defined by part of a conveyor or loading line. Finally, granular material 2 may be defined by building sand or gravel, in which case, container 3 may be defined by a store, or a vehicle, or a cement mixer.

Figure 6:
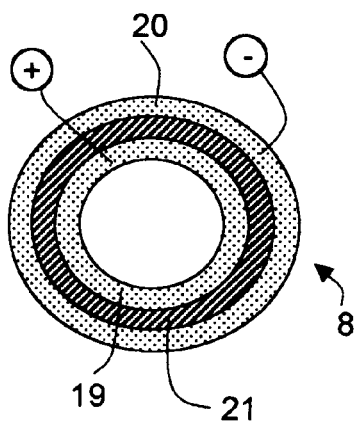
FIG. 6 shows a further geometrical design of the sensitive plates.
Figure 7:
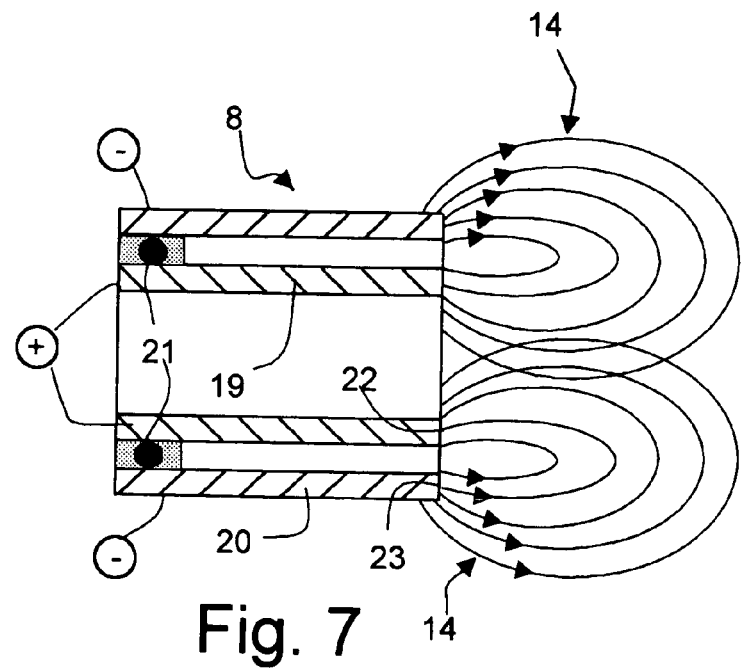
FIG. 7 shows a front view of the FIG. 6 sensor plates.

In the FIGS. 6 and 7 embodiment, the plates of capacitor 8 may be defined by two coaxial cylinders 19 and 20 made of electrically conducting material, separated by a ring 21 of insulating material, and having respective annular edges 22 and 23 defining the outer field 14 region.

Whichever the case, sensor 5, with plates 9, 10 or 19, 20 of any form, is placed inside container 3, in the region in which the compactness of granular material 2 is to be determined; plates 9, 10 or 19, 20 of sensor 5 are shaped to maximize the edge effects in generating the electromagnetic field; and the variation in the capacitive impedance component of sensor 5, when granular material 2 is fed into container 3 and into contact with sensor 5, can be related to the compactness of the granular material.

The variation in the capacitive impedance component of sensor 5, and therefore the compactness of the granular material, are measured by conditioning and control circuit 6, which converts the impedance variation into an electric signal that can be acquired and processed by a computer. One embodiment of the invention employs a resonating circuit, in which case, the impedance variation is related to the frequency of the circuit.

The physical principle and the structures of sensor 5 described above (or other comparable operating structures) therefore allow a wide range of applications, as required in each particular case. The following is a list of preferred, though purely non-limiting, embodiments of sensor 5.

a) Stand-alone sensor 5, e.g. as shown in FIGS. 2, 4, 5 or 6, which has an independent structure, may be of various sizes, can be fitted to the regions of containers 3, or molds or patterns, in which sand compactness is to be evaluated, and, if necessary, can be removed easily for further use.

b) Sensor 5 on a thin, rigid or flexible support, e.g. as shown in FIGS. 2–5, in which plates 9 and 10 may be defined by rigid or flexible plates, possibly on a support 16 in the form of a thin, flexible, adhesive film applied to or incorporated in the pattern or container 3.

c) In situ sensor 5, in particular fitted to clusters of polymer foam for Lost Foam Casting. Using the screen printing or other thin film deposition methods, a structure of interlacing segments or concentric spirals can be formed directly on the surface of the cluster; in which case, sensor 5 may be "disposable". If abrasion by the sand is a problem, sensor 5 may have a protective coating deposited on surfaces 15 of plates 9, 10.

Complex casting patterns can be developed faster and more profitably by equipping critical sand compaction regions with appropriate sensors, thus reducing the risk of errors which would otherwise only be detected after pouring and examining the finished castings. Newly developed parts can also be marketed faster by determining optimum process parameters sooner.

As stated, capacitive sensors 5 according to the present invention may be used to equip casting line formworks, sand core molds, etc. And circuit 6 may be designed for continuous, in situ control of the sand filling and compaction stage, which as yet has never been controlled directly, to prevent the use of less than perfect formworks, and so reduce the number of rejects.

The method of evaluating local compactness of a granular material 2 inside a container 3 therefore comprises the steps of:

setting up a compactness evaluation system 1 comprising a capacitive sensor 5, and a conditioning and control circuit 6 for conditioning and controlling said sensor 5 and capable of evaluating the variation in impedance of sensor 5;

placing said sensor 5 inside a region of said container 3 in which the compactness of said granular material 2 is to be evaluated;

feeding said granular material 2 into said container 3 and into contact with said sensor 5; and directly evaluating, by means of said conditioning and control circuit 6, the local compactness of granular material 2 contacting or in close proximity to said sensor 5, on the basis of the variation in the impedance of said sensor 5, and in particular in the capacitive component of said impedance.

If the compactness values are too low, container 3 can be vibrated to achieve the desired compactness, which can be monitored by evaluation system 1. The compactness evaluation method and system according to the invention may be used in any application requiring compactness control of granular materials, e.g.: lines for conveying and loading granular polymer or ceramic materials; building sand and gravel in stores, or on vehicles, or in cement mixers.

Clearly, changes may be made to the evaluation method and system as described herein without, however, departing from the scope of the accompanying claims.

What is claimed is:

1. A method of preparing a mold, wherein the mold is configured to perform sand casting of molten metal, the method comprising:

preparing a mold surface, wherein the mold surface comprises a pattern having gaps;

providing a sensor system, wherein the sensor system comprises a capacitive sensor, wherein the capacitive sensor is positioned proximate to the pattern, wherein the sensor system is operable to evaluate impedance of the capacitive sensor wherein the sensor system comprises one or more layers of film, wherein the act of positioning the capacitive sensor comprises depositing at least one of the one or more layers of film on the mold surface; and positioning the capacitive sensor proximate to the mold surface.

2. The method of claim 1, further comprising:

adding sand to the mold, wherein at least a portion of the added sand is in contact with or proximate to the capacitive sensor;

compacting the sand; and measuring compactness of the sand, wherein the act of measuring compactness of the sand comprises evaluating impedance of the capacitive sensor.

* * * * *